United States Patent
Herrmann et al.

(10) Patent No.: US 6,872,727 B1
(45) Date of Patent: Mar. 29, 2005

(54) POLYCYCLIC PYRIMIDINE -2,4(1H,3H)-DIONES WITH FUNCTIONALIZED ALKYL RESIDUES AT THE 1- AND/OR 3-POSITION (S); METHODS FOR THEIR SYNTHESIS AND PHARMACEUTICAL PREPARATION

(75) Inventors: Konrad Herrmann, Leipzig (DE); Siegfried Leistner, Leipzig (DE); Petra Wippich, Hamburg (DE)

(73) Assignee: Privates Institut fur Biomedizinische Forschung und Beratung, Leipzig (DE)

( * ) Notice: Subject to any disclaimer, the term of this patent is extended or adjusted under 35 U.S.C. 154(b) by 110 days.

(21) Appl. No.: 09/830,518

(22) PCT Filed: Aug. 21, 2000

(86) PCT No.: PCT/EP00/08126

§ 371 (c)(1), (2), (4) Date: Mar. 15, 2002

(87) PCT Pub. No.: WO01/14344

PCT Pub. Date: Mar. 1, 2001

(30) Foreign Application Priority Data

Aug. 26, 1999 (DE) .......................... 199 40 494

(51) Int. Cl.[7] .......................... A61K 31/517
(52) U.S. Cl. .............. 514/258.1; 514/260.1; 514/266.3; 544/253; 544/278; 544/285
(58) Field of Search ................. 544/278, 285, 544/253; 514/258.1, 260.1, 266.3

(56) References Cited

FOREIGN PATENT DOCUMENTS

| DE | 293816 | 9/1991 |
|---|---|---|
| DE | 293824 | 9/1991 |
| EP | 0454060 | 10/1991 |

OTHER PUBLICATIONS

Leistner et al., Chemical Abstracts, vol. 116:83689, 1992.*
Kluge et al., Chemical Abstracts, vol. 116:53664, 1992.*

* cited by examiner

Primary Examiner—Richard L. Raymond
(74) Attorney, Agent, or Firm—Burns, Doane, Swecker & Mathis, L.L.P.

(57) ABSTRACT

Polycyclic pyrimidine-2,4(1H,3H)-diones with functionalized alkyl residues at the 1-, the 3-, or both position(s); methods for their synthesis, production, and pharmaceutical preparation. The invention concerns the synthesis of the above-described compounds, their chemical and structural characterization, and the analysis of their physiological/pharmacological activities in vitro and in vivo. These goals have been attained by the specification of routes of synthesis, methods for the production of the compounds, and the presentation of compound-specific characteristics. The substances encompassed by the present invention demonstrate pharmacologically significant collangenase/matrix metalloproteinase inhibitory activities. The specific example 1-(3-mercaptoprop-1-yl)-3-methyl-chinazolin-2,4(1H,3H)-dione will be presented in detail.

8 Claims, No Drawings

POLYCYCLIC PYRIMIDINE -2,4(1H,3H)-DIONES WITH FUNCTIONALIZED ALKYL RESIDUES AT THE 1- AND/OR 3-POSITION (S); METHODS FOR THEIR SYNTHESIS AND PHARMACEUTICAL PREPARATION

This application is a 371 of PCT/EP00/08126, filed Aug. 21, 2000.

DESCRIPTION

The invention concerns polycyclic pyrimidine-2,4(1H,3H)-diones with functionalized alkyl residues at the 1- and/or 3-position(s) with the general structures Ia and Ib:

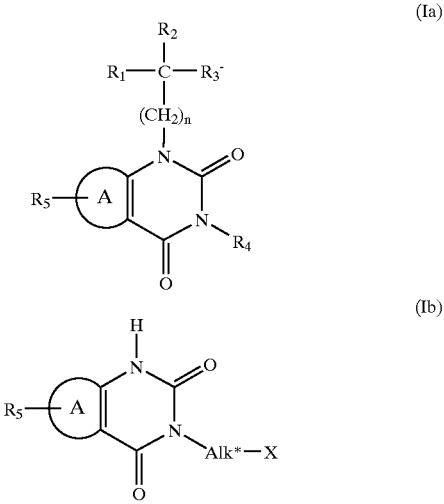

where $R^1$ is a hydrogen, methyl, or ethyl group $R^2$ is a hydrogen or methyl group $R^3$ is a mercapto- or hydroxyaminoacylalkylthio-(—SAlkCONHOH) group Alk is an alkyl group ($C_1$–$C_5$, branched or unbranched)

$R^4$ is a hydrogen, Alk, benzyl, or phenyl group n is 0, 1, or 2

Alk* are alkylenes {$C_4$–$C_{12}$, unbranched or branched, with the exception of 3-methylpropylene [—CH$_2$—CH$_2$—CH(CH$_3$)—]}

X is a mercapto- or hydroxyaminoacylalkylthio-(—SAlkCONHOH) group

A is an annealed benzene ring and $R^5$ is a hydrogen, 6-methyl, 8-methyl, 6-fluoro, 6-chloro, 6-bromo, 6-methylthio, or a 6,7-dimethoxy group, or in the 2,3 positions an annealed thiophene ring, which if necessary is dimethyl-substituted in the 4,5 positions or condensed with a cyclopentene, cyclohexene, or cycloheptene ring, as well as their tautomers and salts, methods for their synthesis and pharmaceutical preparation, especially regarding their applications in diseases of humans and animals, by which the inhibition of collagenases and related metalloproteinases (matrix metalloproteinases, MMPs) is involved in the healing of such diseases, or exerts a palliative effect on the pathological symptoms caused by these enzymes, or interferes with the normal activity of such enzymes to the benefit of the patient.

Compounds with the general structures Ia and Ib have not yet been described in professional literature. One exception is a compound with the general structure Ib with $R^5$=H and Alk*=—CH$_2$CH$_2$—CH(CH$_3$)— and X=SH. This substance is described in EP 0 454 060 as 3-(mercapto-3-methylpropyl)-chinazolin-2,4(1H,3H)-dione with a branched alkyl =$C_4$. It was ascribed immunostimulatory and immunorestorative effects for applications in disorders of the immune system and in viral infections.

In DD 293 816, the applicant presents in structure II a chinazoline in which n=2 and $R^2$=CH$_3$, which may be described as 3-(mercapto-3-methylpropyl)-chinazolin-2,4 (1H,3H)-dione. It served as the starting compound for the synthesis of 3-(alkylthioalkyl)-2,4-dioxo-1,2,3,4-tetrahydrochinazolinene. Similarly, in DD 293 817, methods are described in which compounds shown in structure II with n=2 and $R^2$=CH$_3$, thus 3-(mercapto-3-methylpropyl)-chinazolin-2,4(1H,3H)-dione, serves as a synthetic intermediate.

It is known that the enzymatic activities of metalloproteinases are physiologically regulated by specific activation and inhibitory mechanisms. An uncontrolled enzymatic activation or insufficient inhibition of these enzymes, especially in the case of rheumatic diseases, results in dysregulated cartilage degradation and subsequent chronic and painful pathological changes in the affected articulations.

Another example of the pathological effects of collagenases/MMPs is tumor metastasis and invasion. Secreted collagenases/MMPs degrade dense collagenous connective tissue, allowing the cancerous cells to migrate away from the tumor, to gain access to the circulatory or lymphatic system, to exit that circulation, and to establish metastases in organs distant from the site of the original tumor.

A further medical/cosmetic example of the effects of dysregulated collagenase activity is UV-induced erythema, most commonly induced by excessive/intensive solar irradiation (i.e. sunburn). Collagenases/MMPs in the exposed skin are activated by the UV radiation in sunlight or from tanning devices; these activated enzymes degrade the connective tissue collagen of the skin and blood capillaries, leading to the well-known symptoms of sunburn.

The pathological effects caused by the activities of collagenases/MMPs described in the preceding examples can be prevented by stable inhibitors of these enzymes. It is further likely that specific inhibitors will be able to block only the targeted enzyme, allowing the possibility to interrupt the pathological cartilage destruction characteristic of rheumatoid arthritis with minimal side effects.

Methods for the preparation of compounds with collagenase inhibitory effects have been described. As a rule, these active substances have a peptide backbone based on the structures of natural inhibitors or substrates. These peptide- or pseudopeptide substrate analogues possess an essential zinc-binding group, which chelates the active-site zinc atom in the metal-dependent collagenases/MMPs.

For therapeutic applications, peptide analogue inhibitors have many disadvantages, including inadequate uptake, short biological half-lives, and only limited stability in vivo.

Thus, there is a dear need to develop nonpeptide pharmaceutical inhibitors that lack the above-described disadvantages of the peptide-based collagenase/MMP inhibitors. These new collagenase-inhibiting substances must be biologically stable, readily absorbed, and have a high and specific affinity for the zinc atom in the collagenase/MMP active site.

The purpose of this invention is to discover new nonpeptide chemical substances that possess collagenase/MMP inhibitory activity. It is the further purpose of this invention to develop methods for both the production of such inhibitory substances and the development of pharmaceuticals that contain these substances.

These goals have been suitably achieved. The dependent claims concern advantageous procedural variations of the invention.

The polycyclic pyrimidine-2,4(1H,3H)-diones with functionalized alkyl residues in the 1- and/or 3-posibon described in the invention have the general structures la and lb,

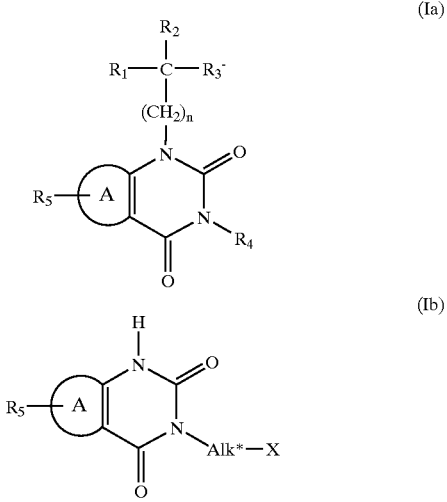

where $R^1$ is a hydrogen, methyl, or ethyl group $R^2$ is a hydrogen or methyl group $R^3$ is a mercapto- or hydroxyaminoacylalkylthio-(—SAlkCONHOH) group Alk is an alkyl group ($C_1$–$C_5$, branched or unbranched)

$R^4$ is a hydrogen, Alk, benzyl, or phenyl group n is 0, 1, or 2

Alk* are alkylenes {$C_4$–$C_{12}$, unbranched or branched, with the exception of 3-methylpropylene [—$CH_2$—$CH_2$—$CH(CH_3)$—]}

X is a mercapto- or hydroxyaminoacylalkylthio-(—SAlkCONHOH) group

A is an annealed benzene ring and $R^5$ is a hydrogen, 6-methyl, 8-methyl, 6-fluoro, 6-chloro, 6-bromo, 6-methylthio, or a 6,7-dimethoxy group, or in the 2,3 positions an annealed thiophene ring, which if necessary is dimethyl-substituted in the 4,5 positions or condensed with a cyclopentene, cyclohexene, or cycloheptene ring.

The invention explicitly concerns the core compounds described in the invention, their tautomers and their salts, particularly those salts most appropriate for pharmacological applications such as sodium and ammonium.

The compounds described by structures la and lb are novel chemical substances with enzyme inhibitory, specifically collagenase/MMP inhibitory qualities, which allows them to be applied to great advantage in human and veterinary medicine. Furthermore, these novel substances readily lend themselves to further chemical modification to produce compounds with analogous or altered spectra of activity.

Of the many compounds with the general structures la and lb, special emphasis is placed on the development of compounds with structures IIa and IIb:

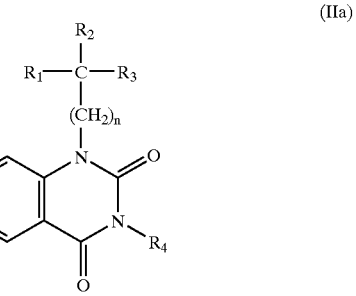

where $R^1$, $R^2$, $R^3$, $R^4$, Alk, Alk*, n, and X are defined as above.

Comprised in the present invention are compounds with the general structures Ia and Ib either as such or as their tautomers, or as their salts, particularly pharmaceutically harmless alkali or ammonium salts.

The methods described in the invention for the preparation of the compounds with the general structures Ia, where $R^3$ and $R^4$ are a mercapto group and a hydrogen, respectively, are characterized by the following procedure:

(A) the reaction of 2-(alkenylaminoy)-1-carboxylic acid amide with the general structure III,

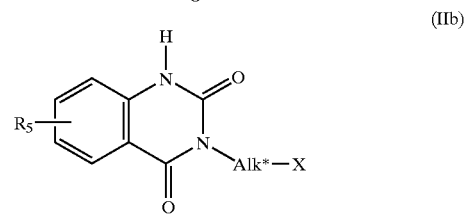

where $R^6$ is an alkenyl group ($C_3$–$C_6$) such as allyl, methallyl, crotyl, 1-butene-4-yl, 3-pentene-1-yl, or 3-hexene-1-yl, and A and $R^5$ are defined as above, with a reagent providing a (—C=S—) structural element such as thiophosgene, thiourea, ammonium or alkalithiocyanate/HCl, 1,1'-thiocarbonylbisimidazole, or benzoylisothiocyanate in a polar, aprotic solvent.

stir the reaction mixture remove solvent under vacuum add dilute alkali solution and gently heat to circa 60° C., separate the insoluble fraction by filtration, cool and acidify the filtrate, heat the resulting compound with the general structure IV,

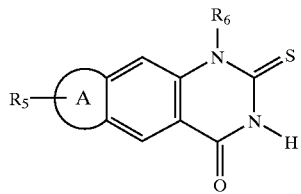
(IV)

where A, $R^5$, and $R^6$ are as defined above,
  with centrated mineral acid, such as hydrochloric acid, hydrobromic acid and/or sulfuric acid, or a mixture of these mineral acids with glacial acetic acid and/or formic acid to reflux, cool the reaction mixture,
dry the resulting compound with the general structure V,

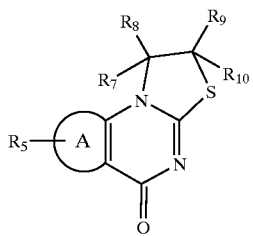
(V)

where $R^7$, $R^8$, $R^9$, and $R^{10}$ are hydrogen, a methyl, or an ethyl group and A and $R^5$ are as defined above,
  or respectively, dry the resulting compound with the general structure VI,

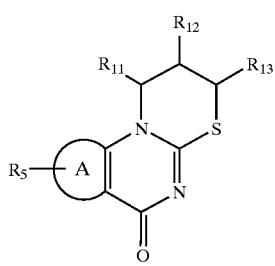
(VI)

where $R^{11}$, $R^{12}$, and $R^{13}$ are a hydrogen, a methyl, or an ethyl group, and A and $R^5$ are as defined above,
  in a vacuum desiccator over potassium hydroxide or
  stir the above compound in a dilute, aqueous sodium carbonate solution,
  isolate the compound,
  warm the compound in dilute mineral acid, such as hydrochloric acid, hydrobromic acid and/or sulfuric acid, or a mixture of these mineral acids with glacial acetic acid and/or formic acid to reflux,
  cool the reaction mixture,
  wash and dry the crystallized material, yielding the compound with the general structure Ia or its tautomers, in which $R^4$ is without exception hydrogen.

The method described in the invention for the preparation of the compounds with the general structure Ia, where $R^3$ is a mercapto group, $R^4$ is a hydrogen, benzyl, or phenyl group, n=1 or 2, and Alk, A, and $R^5$ are as defined above, is characterized by the following procedure:

B) the reaction of bi- and tricyclic 3-alkyl (resp. benzyl or phenyl)-pyrimidine-4(3H)-on-2(1H)-thionene with the general structure VII,

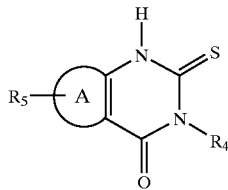
(VII)

where R4 is a hydrogen, an alkyl, a benzyl or a phenyl group, and A and $R^5$ are defined as above,
with 1,ω-dihalogenalkanene with the general structure VIII, $$Hal(CH_2)_mHal \quad (VIII)$$

where m=2, 3, or 4, and Hal is chlorine, bromine, or iodine,
  In an aprotic dipolar solvent, preferably in dimethylformamide with the addition of potassium carbonate with gentle stirring at room temperature,
  add dilute hydrochloric acid,
  heat until reflux,
  filter the hot reaction mixture,
  cool and store the solution at 4° C.,
  yielding the compound with the general structure Ia,
where $R^3$ is a mercapto, $R^4$ a hydrogen, a benzyl, or a phenyl group, and A and $R^5$ are as defined above, or
C) the reaction of 2-ammonium carboxylic acid methyl ester thiocyanate with the general structure IX,

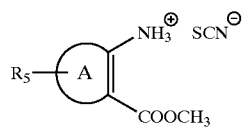
(IX)

where A and $R^5$ are as defined above,
with 1,ω-dihalogenalkanene with the general structure VIII,
where m=2 or 3 and Hal is chlorine, bromine, or iodine,
  heat the reactants with stirring until reflux
  cool and isolate the precipitate,
  wash the precipitate with diethylether and dry,
  dissolve the precipitate in water,
  filter the solution and add dilute aqueous NaOH to pH 10,
  isolate the precipitate and wash with water,
  dry the precipitate with vigorous shaking with chloroform,
  isolate the precipitate and dry.
  Recrystallize from solvent, preferably 2-methoxyethanol yielding compounds of the general structure V,
  obtained by reaction with 1,3-dibromomethane,
  where $R^7$, $R^8$, $R^9$, and $R^{10}$ are hydrogen and A and $R^5$ are as defined above,
  or the compound of the general structure VI,
  obtained by reaction with 1,3-dibromopropane
  where $R^{11}$, $R^{12}$, and $R^{13}$ are hydrogen, and A and $R^5$ are as defined above.
  Heat the compounds of the general structures V or VI in dilute mineral acid, such as hydrochloric acid, hydrobromic acid and/or sulfuric acid, or a mixture of these mineral acids with glacial acetic acid and/or formic acid to reflux,
  cool the reaction mixture, wash and dry the crystallized material to yield a compound of the general structure Ia or its tautomers, where $R^1, R^2$, and $R^4$ are hydrogens, $R^3$ is a mercapto group, n=1 or 2, and A and $R^5$ are as defined above.

The methods described in the invention for the preparation of the compounds with the general structure 1b, where Alk* is n-butylene (—$CH_2$—$CH_2$—$CH_2CH_2$—), X is a mercapto group, and A and $R^5$ are as defined above, are characterized by the following procedures:

D) React 2-isothiocyanato-1-carboxylic acid ester of the general structure X,

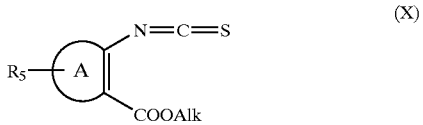

where Alk, A, and $R^5$ are defined as above,
with 4-aminobutan-1-ol at room temperature with vigorous and prolonged stirring
add water to obtain the compounds of the general structure XI,

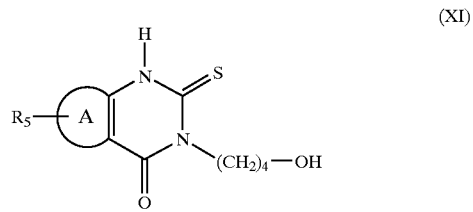

where A and $R^5$ are as defined above,
react the compounds of the general structure XI with concentrated mineral acid, such as hydrochloric acid, hydrobromic acid and/or sulfuric acid, or a mixture of these mineral acids with glacial acetic acid and/or formic acid to reflux,
cool the reaction mixture and isolate the crystallized material,
add aqueous sodium carbonate to the crystals to obtain ca. pH 9,
isolate the crystallized material, wash with water, and dry to obtain the polycyclic 2,3,4,5-tetrahydro-7H-[1,3]thiazepino[2,3-a]pyrimidin-7-one of the general structure XII,

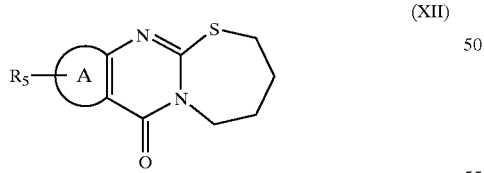

where A and $R^5$ are as defined above.

Heat the compounds of the general structures XII in very dilute mineral acid, such as hydrochloric acid, hydrobromic acid and/or sulfuric acid, or a mixture of these mineral acids with glacial acetic acid and/or formic acid to reflux,
cool the reaction mixture,
wash and dry the crystallized material to obtain compounds of the general structure Ib or its tautomers where
Alk* is n-butylene (—$CH_2$—$CH_2$—$CH_2$—$CH_2$—), X is a mercapto group, and A and $R^5$ are as defined above.

The methods described in the invention for the preparation of the compounds with the general structure 1b, where Alk* is alkylene ($C_4$–$C_{12}$; unbranched and branched, with the excepton of 3-methylpropylene [—$CH_2$—$CH_2$—CH($CH_3$)—], X is a mercapto group, and A and $R^5$ are as defined above, are characterized by the following procedures:

E) React 2-alkoxycarbonylamino-1-carboxylic acid alkyl ester of the general structure XIII,

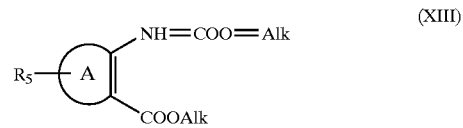

where Alk is an alkyl group ($C_1$–$C_3$) and A and $R^5$ are as defined above, with aminoalkanols of the general structure XIV,
where Alk* is alkylene {$C_4$–$C_{12}$; unbranched and branched, with the exception of 3-methylpropylene [—$CH_2$—$CH_2$—CH($CH_3$)—]}by warming in a well-known reaction,
cool the reaction mixture,
add water and dilute hydrochloric acid to ca. pH 4,
isolate the precipitate, wash with water and dry to yield the polycyclic 3-(ωhydroxyalkyl)-pyrimidine-2,4(1H,3H)-diones with the general structure XV,

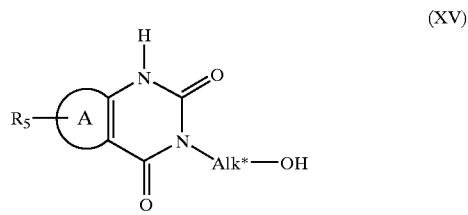

where Alk* is alkylene {$C_4$–$C_{12}$; unbranched and branched, with the exception of 3-methylpropylene [—$CH_2$—$CH_2$—CH($CH_3$)—]} and A and $R^5$ are as defined above.

React the compounds with the general structure XV with concentrated hydrochloric acid, phosphorus trichloride, or phosphorus oxide chloride; preferably, however, with hydrobromic acid:
heat to reflux,
cool the reaction mixture,
isolate the precipitate, wash with water, and dry to yield the polycyclic 3-(ω-haloalkyl)-pyrimidine-2,4(1H,3H)-diones with the general structure XVI,

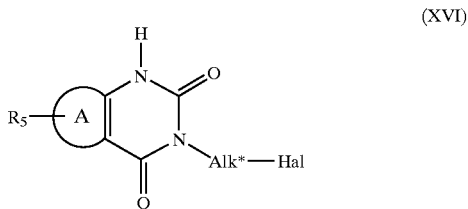

where Hal is chlorine, or bromine, and Alk*, A, and $R^5$ are as defined above.

React the compounds of the general structure XVI in boiling polar solvent with thiourea:
heat to reflux,
cool the reaction mixture, add water and dilute sodium hydroxide to obtain an alkaline pH value, after clearing the solution by filtration, add dilute hydrochloric acid to ca. pH 3,0, isolate the precipitate, what with water and dry to yield compounds with the general structure Ib and its tautomers where Alk* is alkylene {$C_4$–$C_{12}$; unbranched and branched, with the exception of 3-methylpropylene [—$CH_2$—$CH_2$—$CH(CH_3)$—]}, X is a mercapto group, and A and $R^5$ are as defined above.

The methods described in the invention for the preparation of compounds with the general structures 1a or 1b, where $R^3$ or X is a hydroxyaminoacylalkylthio (—SAlkCONHOH) group and $R^1$, $R^2$, $R^4$, Alk, n, Alk*,A, and $R^5$ are as defined above, are characterized by the following procedures:

F) React compounds with the general structures Ia or Ib, where $R^3$ is a mercapto group, and $R^1$, $R^2$, $R^4$, Alk, n, Alk*,A, and $R^5$ are as defined above, with N-hydroxyhalogen carboxylic add amides, preferably 2-choro-N-hydroxyacetamide ($ClCH_2CONHOH$), in pyridine or in acetone solution, preferably in the presence of a base, at room temperature, distill away the solvent, add water, isolate the precipitate, wash with water and dry to yield compounds of the general structure Ia or Ib or their tautomers, where $R^3$ or X is a hydroxyaminoacylalkylthio group.

According to the present invention, the procedures designated (A–H) may be modified.

For example, further procedures regarding the invention described in method (A) include:

the reaction of the compounds with the general structure III with benzoylisothiocanate in absolute acetone, in the execution of method (B), another procedure included in the invention is that the reaction of compounds of the general structure VII with compounds of the general structure VIII may be carried out in absolute dimethylformamide in the presence of dry potassium carbonate.

Studies of Collagenase/MMP Inhibitory Effects

TABLE 1

Inhibition of human matrix metalloproteinases and *Clostridium histolyticum* collagenase by compounds based on the general structures Ia and Ib

| | Lead compound | MMP-2 (50% inhibition) | MMP-8 ($K_i$ value) | MMP-9 (50% inhibition) | *C. histolyticum* (50% inhibition) |
|---|---|---|---|---|---|
| Example 1 | (Ia) | 23.3 µM | 33.3 µM | | 21.0 µM |
| Example 2 | (Ia) | 142.9 µM | negative | | |
| Example 3 | (Ia) | 13.2 µM | 38.5 µM | negative | 27.5 µM |

TABLE 1-continued

Inhibition of human matrix metalloproteinases and *Clostridium histolyticum* collagenase by compounds based on the general structures Ia and Ib

| | | Lead compound | MMP-2 (50% inhibition) | MMP-8 ($K_i$ value) | MMP-9 (50% inhibition) | *C. histolyticum* (50% inhibition) |
|---|---|---|---|---|---|---|
| Example 4 | [structure] | (Ia) | 5.0 μM | 7.0 μM | 6.0 μM | 53.8 μM |
| Example 5 | [structure] | (Ia) | 61.3 μM | 70.0 μM | 12.5 μM | 39.2 μM |
| Example 6 | [structure] | (Ia) | 97.1 μM | negative | | 13.1 μM |
| Example 7 | [structure] | (Ia) | 6.0 μM | negative | 71.4 μM | 11.5 μM |
| Example 8 | [structure] | (Ia) | | negative | | 39.4 μM |
| Example 9 | [structure] | (Ia) | 13.9 μM | | 43.4 μM | |

TABLE 1-continued

Inhibition of human matrix metalloproteinases and *Clostridium histolyticum* collagenase by compounds based on the general structures Ia and Ib

| | Lead compound | MMP-2 (50% inhibition) | MMP-8 ($K_i$ value) | MMP-9 (50% inhibition) | *C. histolyticum* (50% inhibition) |
|---|---|---|---|---|---|
| Example 10 | (Ia) | 6.3 μM | | | 31.5 μM |
| Example 11 | (Ia) | | 33.3 μM | | 22.4 μM |
| Example 12 | (Ib) | 8.3 μM | 11 μM | 20 μM | |
| Example 13 | (Ib) | | 20 μM | | |
| Example 14 | (Ia) | 20 μM | negative | 50 μM | |
| Example 17 | (Ia) | 20 μM | negative | 10 μM | |

TABLE 1-continued

Inhibition of human matrix metalloproteinases and *Clostridium histolyticum* collagenase by compounds based on the general structures Ia and Ib

| | Lead compound | MMP-2 (50% inhibition) | MMP-8 ($K_i$ value) | MMP-9 (50% inhibition) | C. histolyticum (50% inhibition) |
|---|---|---|---|---|---|
| Example 18 | (Ib) | 8.3 μM | 6.0 μM | 10 μM | |
| Example 19 | (Ib) | 7.1 μM | 3.0 μM | | |
| Example 20 | (Ia) | | | | 71.4 μM |

Inhibition of *Clostridium histolyticum* Collagenase (EC 3.4.24.3)

The activity of *Clostidium histolyticum* collagenase may be readily determined by a simple spectrophotometric assay using the synthetic chromogenic peptide substrate N-(3-[2-furyl]acryloyi)-leucine-glycine-proline-alanine (FALGPA; Van Hart, H. E. and Steinbrink, D. R. 1981, Anal. Biochem. 113, 356). The degree of inhibition of the degradation of this chromogenic substrate by the addition of the various test substances described in Table 1 may be easily quantified. The enzyme and substrate are commercially available.

Inhibition of Human Matrix Metalloproteinase-2 (MMP-2; gelatinase A)

MMP-2 is easily prepared by standard procedures from the culture medium of cultivated human fibroblasts in reasonable quantities, and is therefore readily available. The inactive secreted pro-form (pro-MMP-2) can be activated by the addition of trypsin or by the addition of organomercurial compounds to prepare the enzymatically active mature form of the enzyme. A screening system based on the measurement of the proteolytic activity of MMP-2 was developed to analyse the inhibitory effects of the various inhibitors described in Table 1.

To this end, human dermal fibroblasts were obtained and maintained in culture using standard methods. The cell-free culture supernatant containing the secreted pro-MMP-2 was treated with trypsin. The trypsin was inactivated with the specific active-site serine proteinase inhibitor Nα-p-tosyl-L-lysine-chloromethylketone (TLCK), and the active MMP-2 was partially purified by gel filtration on Sepharose 4B. The isolated MMP-2 was identified and characterized by the use of a commercially available immunoassay.

A simple nonradioactive assay was developed to measure MMP-2 activity using gelatin as a substrate that allows both a large number of samples to be analysed in parallel and to generate kinetic data. Partially purified MMP-2 was incubated with a suitable dilution of gelatin under standardized conditions (time, buffer, pH, temperature, inhibitor, additives), and uncleaved gelatin was separated from degradation products by suction filtration through a nitrocellulose filter. High-molecular-weight gelatin is thereby bound to the nitrocellulose filter, and the low-molecular-weight gelatin-derived peptides pass through it. The nitrocellulose-bound gelatin can be stained with Ponceau S or Commassie Brilliant Blue protein stains, and the degree of staining quantified densitometrically using a commercially available electrophoresis gel documentation system supported by dedicated analytical software. The nitrocellulose filtration is conducted using a commercially available dot- or slot-blotting apparatus.

The gelatinase assay described here has been validated by comparison with results obtained with an established collagenase assay using radioactive or fluorescently labeled collagen as substrate.

Preparation of Human Matrix Metalloproteinase-9 (MMP-9; Gelatinase B)

Native MMP-9 was reproducibly obtained with reasonable yield and purity from human buffy coat. Buffy coat, to which was added an appropriate volume of 10% (v/v) Triton-X-100 to obtain a final concentration of 0,4% detergent, was shaken on ice for 30 min; then, one volume of twofold-concentrated binding buffer (40 mM Tris-HCl pH 7,5, 10 mM $CaCl_2$, 1 M NaCl, 0,2% (v/v) Triton X-100 was added and the mixture shaken on ice for a further 30 min.

The mixture was then centrifuged for 15 min at 16,000 rpm (30,590×g) in a Kendro SS-34 rotor at 4° C. and the resulting supernatant filtered over glass wool. The filtrate was incubated batchwise with gelatin-agarose equilibrated in binding buffer for 1 h on ice with continuous shaking The MMP-9-bound gelatin-agarose was then loaded into a chromatographic tube and the column washed with at least ten bed volumes of binding buffer, or until no protein was detected by absorbance at 280 nm in the wash buffer. MMP-9 was eluted from the gelatin affinity column by application of two bed volumes of binding buffer containing 5% (v/v) dimethylsulfoxide (DMSO).

The eluate was applied to a gel filtration column of Sephadex G-75 both to exchange buffer and to eliminate small amounts of contaminating MMP-2. The G-75 column was prepared and eluted with Buffer I [20 mM Tris-HCl pH 7,5, 5 mM $CaCl_2$, 100 mM NaCl, 0,1% (v/v) Triton X-100].

The eluted MMP-9 includes the three characterized forms of the enzyme: monomer, homodimer, and heterodimer (complex with lipokalin). The purity of MMP-9 was estimated to be ca. 90%, with the remaining contaminating protein being fibronectin and small amounts of TIMPS.

The latent MMP-9 was activated by a 30–60 min incubation at 37° C. with 1/100 vol trypsin (10 mg $ml^{-1}$). The trypsin was subsequently inactivated by addition of the serine proteinase inhibitor phenylmethylsulfonylfluoride (PMSF) or the more specific trypsin inhibitor TLCK.

Cloning of the Gene and Expression of the Catalytic Domain of Human Matrix Metalloproteinase-8 (MMP4; Neutrophil Collagenase)

The catalytic domain of MMP-8 was chosen as a further test enzyme because of its high stability and constitutive activity, obviating the need for enzymatic or chemical activation, which is a well-known source of error, e.g. the commonly used organomercurial compounds used to activate pro-MMPs may interfere in subsequent assays or affect the activity of the enzyme, leading to erroneous interpretation of results. The cloning strategy was designed to express heterologously only the catalytic domain, rather than the entire MMP-8, in *Escherichia coli*. With the so-constructed expressed catalytic domain, we obtained a stable enzymatically active, highly pure enzyme that is well suited for routine investigation of the efficacy of the synthetic inhibitors and provides highly reproducible test results.

The cloning and expression of the recombinant catalytic domain of MMP-8 follows the protocol developed by Schnierer et al. (Schnierer, S., Kleine, T., Gote, T., Hilleman, A., Knäuper, V., and Tschesche, H., 1993, The recombinant catalytic domain of human neutrophil collagenase lacks type I collagen substrate specificity, Biochem. Biophys. Res. Commun. 191, 319–326).

Quantitative Fluorimetric Assay for Matrix Metalloproteinases

The enzymatic cleavage of commercially available synthetic internally quenched fluorigenic peptide substrates such as 7-methylcoumarin-4-yl-acetyl-prolyleucyl-glycyl-leucyl-(dinitrophenyl-L-α,β-diaminopropionyl)-alanyl-arginylamide (Mca-Pro-Leu-Gly-Leu-Dap(Dnp)-Ala-Arg-$NH_2$) at the scissile -Gly-Leu-peptide bond separates the fluorescent Mca group from the dinitrophenol quencher, resulting in a strong linear increase in fluorescence intensity that can be readily measured in a fluorimeter ($\lambda_{exitation}$ 328 nm, $\lambda_{emission}$ 393 nm) over the first few minutes of the reaction. The specificity of the assay for matrix metalloproteinases is provided by the type I collagen-derived sequence -Pro-Leu-Gly-Leu- in the synthetic substrate, as well as by the incubation conditions. To test the efficacy of the synthetic collagenase/MMP inhibitors, the residual enzymatic activity remaining after an incubation of enzyme plus different amounts of inhibitor is measured at a fixed enzyme and substrate concentration. For each inhibitor, three test series at different fixed substrate concentrations were carried out. From the time-dependent increase in fluorescence intensity measured, the velocity (v) of the enzymatic activity can be calculated as increase in arbitrary fluorescence intensity units per minute. The inhibition constant Ki is calculated graphically by the method of Dixon (1953) by plotting the reciprocal of the reaction velocity 1/v on the ordinate, and the inhibitor concentration on the abscissa. The x-intercept of the linear plot is defined as minus $K_1$ value.

Assay

Materials

1984 μl assay buffer (100 mM Tris-HCl pH 7,5, 100 mM NaCl, 10 mM $CaCl_2$, 0,05% Brij 35)

2 μl inhibitor dissolved in DMSO, or DMSO alone as a solvent control

4 μl enzyme (MMP-2, MMP-9, or the catalytic domain of MMP-8)

10 μl Mca-Pro-Leu-Gly-Leu-Dap(Dnp)-Ala-Arg-$NH_2$ in DMSO

Method

1. Incubate buffer, enzyme, and inhibitor for 5 min at room temperature, with stirring.
2. Start the reaction by adding 10 μl substrate in DMSO
3. Record the increase in fluorescence intensity over 2 min.

Confirmation of the Inhibitory Activity by Protein Zymographic Analysis

Zymography permits the rapid and simple analysis of complex mixtures of proteinases. A protease substrate, usually a protein like casein, fibrinogen, or gelatin, is co-polymerized in a polyacrylamide gel and the enzyme mixture to be analysed is electrophoretically separated in the gel. After the electrophoresis is complete, the gel is incubated in a suitable buffer to allow the separated proteolytic enzymes to digest the immobilized substrate. After fixation and staining, colorless bands appear on a stained substrate background; the dear bands indicate the position on the gel where the separated proteinases have digested the substrate.

The compounds found to be effective collagenase inhibitors by fluorimetric analysis were analysed on gelatin-containing polyacrylamide gels. The potential inhibitors may either be co-polymerised in the gel with the gelatin substrate or applied with the enzyme after a suitable incubation prior to electrophoresis. This is possible because the test compounds, in contrast to the collagenases/MMPs, are not charged (below the pK value of the —SH group) and therefore do not migrate alone during the electrophoresis.

By this method, crude samples containing collagenase/MMP activity can be analysed. The effects of the novel compounds on collagenase/MMP activities in cell culture supernatant, synovial fluid, and tissue extracts can be tested by zymographic analysis. Metalloproteinases can be identified in complex mixtures containing other proteolytic enzymes by inhibition with the zinc chelator 1,10-

EXAMPLE 1

(R,S)-1-mercaptopropyl)-chinazolin-2,4(1H,3H)-dione
(structure 1a, $R^1$=hydrogen, $R^2$=methyl, $R^3$=mercapto, $R^4$=hydrogen, n=1, A=benzene ring with $R^5$=hydrogen)

a) 2 allylaminobenzoic acid amide (structure III, $R^6$=allyl, A=benzene ring with $R^5$=hydrogen)

2-aminobenzamide (13,60 g; 0,1 mol) is suspended in 80 ml water, to which is added 6,90 g potassium carbonate and 7,70 g (0,1 mol) allylchloride. The reaction mixture is then refluxed for 2 h. After cooling, crystals are precipitated from ehtanol/water (1:1, v/v). Between 13,8 and 14,3 g colourless crystals of 2-allylbenzoic acid amide are obtained.
Yield 79%.
$C_{10}H_{12}N_2O$ (176,2).
F.: 88°–92° C. (ethanol/water).

b) 1-allylchinazolin-4(3H)-on-2-(1H)-thione (structure IV, $R^6$=allyl, A=benzene ring with $R^5$=hydrogen)

The thin-layer chromatographically-pure compound described in (a) (8,81 g; 0,05 mol) is dissolved in 50 ml acetone and reacted with 0,06 mol benzoytisothiocyanate. The reaction mixture is stirred at room temperature for 24 h, after which the solvent is removed under vacuum. With constant stirring, 50 ml water is added to the residue, and then 10% aqueous sodium hydroxide is added to pH 9. With further stirring, the suspension is heated slowly to 60° C. and the small amount of insoluble material is eliminated by filtration. After cooling, the solution is acidified with 10% aqueous hydrochloric acid. The precipitate is collected by filtration, washed with water, and after drying, recrystallized to obtain 5,35 light yellow crystals of 1-allylchinazolin-4(3H)-on-2(1H)-thione.
Yield 49%.
$C_{11}H_{10}N_2OS$ (218,3).
F.:179°180° C. (ethanol).
IR (v in cm$^{-1}$): 1608 (NH), 1692 (C=O), 2948 ($CH_2$).
MS m/e (% B): $M^+$218(27), 203(100), 119(21), 77(33).

c) (R,S)-2-methyl-1,2-dihydro-5H-thiazolo[3,2-a]chinazolin-5-one hydrobromide (structure V, $R^7$=$R^8$=$R^{10}$=hydrogen, $R^9$=methyl, A=benzene ring with $R^5$=hydrogen)

The thin-layer chromatographically-pure compound described in (b) (2,18 g; 0,01 mol) is refluxed in 20 ml concentrated hydrobromic add for 30 min. After cooling, the precipitate retained on a glass frit is dried in a vacuum desiccator over potassium hydroxide. The final product obtained is 1,67 g thin-layer chromatographically-pure colourless crystals of (R,S)-2-methyl-1,2-dihydro-5H-thiazolo[3,2-a]chinazolin-5-one hydrobromide.
$C_{11}H_{10}N_2OSxHBr$ (298,3+xHBr).
F.: 242°247° C. (ethanol).
IR (v in cm$^{-1}$): 1618 (C=N), 1686 (C=O), 2922 ($CH_2$).
MS m/e (% B): $M^+$218(100), 203(13), 190(49), 175(17).

d) (R,S)-1-(2-mercaptopropyly)-chinazolin-2,4(1H,3H)-dione (structure 1a, $R^1$=hydrogen, $R^2$=methyl, $R^3$=mercapto, $R^4$=hydrogen, n=1, A=benzene ring with $R^5$=hydrogen)

The compound described in (c) (1,50 g) is refluxed in a mixture of 0,6 ml concentrated sulfuric acid, 1,5 ml glacial acetic acid, and 66 ml water for 8 h. After cooling, the precipitate obtained on a glass frit is washed with a small amount of water, and after drying, recrystallized to yield 1,05 g colorless crystals of (R,S)-1-(2-mercaptopropyl)-chinazolin-2,4(1H,3H)-dione.

$CH_{11}H_{12}N_2O_2S$ (236,3).
F.: 170°–173° C. (ethanol).
IR (v in cm$^{-1}$): 1608 (NH), 1682 (C=O), 1702 (C=O), 2554 (SH), 2922 ($CH_2$).
MS m/e (% B): $M^+$236(6), 204(21), 176(17), 162(89), 149(34), 132(100).
$UV_{ethanol}$(in nm) (log E): 220,2 (4,83), 244,2 (4,22), 310,8 (3,94).

EXAMPLE 2

1-(2-mercapto-2-methylpropyl)-chinazolin-2,4(1H,3H)-dione
(structure 1a, $R^1$=$R^2$=methyl, $R^3$=mercapto, $R^4$=hydrogen, n=1, A=benzene ring with $R^5$=hydrogen).
Colorless crystals.
Yield 76% based on the last step of the synthesis.
$C_2H_{14}N_2O_2S$ (250,3).
F.: 183°186° C. (ethanol).
IR (v in cm$^{-1}$): 1610 (NH), 1684 (C=O), 1712 (C=O), 2552 (SH), 2928 ($CH_2$).
MS m/e (% B): $M^+$+1 251(100), $M^+$250(8), 217(9), 176(58), 162(33), 149(100), 132(50).
$UV_{ethanol}$(in nm) (log ε): 220,0 (4,36), 245,2 (3,80), 312,2 (3,61).

The preparation of this mercapto derivative is analogous to that described in Example 1; nevertheless the following intermediates were isolated and characterized:

a) 2-methallylamino benzoic acid amide (structure III, $R^6$ methallyl, A=benzene ring with $R^5$=hydrogen).
Prepared from 2-aminobenzamide and methallylchloride.
Colorless crystals.
Yield 87%.
$C_{11}H_{14}N_2O$ (190,2).
F.: 130° C. (ethanol/water).
IR (vin cm$^-$): 1622 asymm.(NH, C=O), 2910 ($CH_2$).
MS m/e (% B): $M^+$190(50), 173(86), 158(19), 144(47), 132(100).

b) 1-methallylchinazolin-4(3H)-on-2(1 H)-thione (structure IV, $R^6$=methallyl, A=benzene ring with $R^5$=hydrogen).
Prepared from 2-methallylamino benzoic acid amide and benzylisothiocyanate in absolute acetone solution.
Light yellow crystals.
Yield 53%.
$C_{12}H_{12}N_2OS$ (232,3).
F.: 181°–182° C. (ethanol).
IR (vin cm$^{-1}$): 1606 (NH), 1682 (C=O), 2930 ($CH_2$).
MS m/e (% B): $M^{+232}$(31), 217(100), 199(27), 184(11), 119(13).

c) 2,2-dimethyl-1,2-dihydro-5H-thiazolo[3,2-a]chinazolin-5-one (structure V, $R^7$=$R^8$=hydrogen, R9=$R^{10}$=methyl, A=benzene ring with $R^5$=hydrogen).
Prepared from 1-methallylchinazolin-4(3H)-on-2(1H)-thione and concentrated hydrobromic acid. The precipitate obtained after cooling is resuspended in 5% aqueous sodium carbonate at room temperature.
Colorless crystals.
Yield 87%.
$C_{12}H_{12}N_2OS$ (232,3).
F.: 269° C. (ethanol).
IR (vin cm$^{-1}$): 1618 (NH), 1684 (C=O), 2923 ($CH_2$).
MS m/e (% B): $M^+$232(100), 217(15), 204(18), 189(38), 171(26).
$UV_{ethanol}$(in nm) (log ε): 234,0 (4,31), 254,5 (4,38), 309,5 (3,90).

The reaction of the compound obtained in step (c) analogous to the method described under (1d) yields 1-(2-mercapto-2-methyl-propylychinazolin-2,4(1H,3H)-dione.

EXAMPLE 3

(R,S)-1-(3-mercaptobut-1-yl)-chinazolin-2,4(1H,3H)-dione (structure 1a, $R^1=R^4$=hydrogen, $R^2$=mercapto, $R^3$=methyl, A=benzene ring with $R^5$=hydrogen).
Colorless crystals.
Yield 86% based on the last step of the synthesis.
$C_{12}H_{14}N_2O_2S$ (250,3).
F.: 142°143° C. (ethanol).
IR (ν in $cm^-$): 1610 (NH), 1680 (C=O), 1694 (C=O), 2554 (SH).
MS m/e (% B): $M^++1$ 251(100).

The preparation of this compound is analogous to Example 1; nevertheless, the following intermediates were isolated and characterized:

a) 2-(but-1-en-4-yl-amino)-benzoic acid amide [structure III, $R^6$=—$(CH_2)_2CH=CH_2$, A=benzene ring with $R^5$=hydrogen].
Prepared from 2-aminobenzamide and 4-bromo-1-butene.
Colorless crystals.
Yield 59%.
$C_{11}H_{14}N_2O$ (190,2).
F.: 114°–115° C. (ethanol).
IR (ν in $cm^{-1}$): 1622 (C=O), 2930 ($CH_2$), 2942 ($CH_2$).
MS m/e (% B): $M^+$190(15), 149(46), 132(100).

b) 1-(but-en-4-yl)-chinazolin-4(3-on-2(1H)-thione [structure IV, $R^6$=$(CH_2)_2CH=CH_2$. A=benzene ring with $R^5$=hydrogen].
Prepared from 2-(but-1-en-4-yl-amino)-benzoic acid amide and benzylisothiocyanate in absolute acetone solution.
Light yellow crystals.
Yield 39%.
$C_{12}H_{12}N_2OS$ (232,3).
F.: 184°–185° C. (ethanol).
IR (ν in $cm^{-1}$): 1608 (NH), 1682 (C=O), 2950 ($CH_2$).
MS m/e (%B): $M^+$232(35), 203(74), 178(53), 162(8), 145 (12), 132(29), 120(100).

c) (R,S)-3-methyl-2,3-dihydro-1H,6H-[1,3]thiazino[3,2-a] chinzolin-6-one (structure VI, $R^{11}=R^{12}$=hydrogen, R13=methyl, A=benzene ring with $R^5$=hydrogen).
Prepared from 1-(but-en-4-yl)-chinazolin-4(3H)-on-2 (1H)-thione and concentrated hydrobromic acid.
After cooling the reaction mixture, the resulting precipitate is resuspended in 5% sodium carbonate at room temperature, filtrated and dried.
Colorless crystals.
Yield 84%.
$C_{12}H_{12}N_2OS$ (232,3).
F.: 198 –201° C. (ethanol).
IR (ν in $cm^{-1}$): 1636 (C=N), 1708 (C=O), 2926 ($CH_2$), 2962 ($CH_2$).
MS m/e (% B): $M^+$232(100), 204(77), 162(36), 132(46).
$UV_{ethanol}$ (in nm) (log ε): 230,5 (4,27), 257,5 (4,46), 305,5 (3,94).

The reaction of the compound obtained in step (c) analogous to the method described under (1d) yields (R,S)-1-(3-mercaptobut-1-yl)-chinazolin-2,4(1H,3H)-dione.

EXAMPLE 4

1-(3-mercaptopropyl)-chinazolin-2,4(1H,3H)-dione (structure 1a, R1=R2=R4=hydrogen, R3=mercapto, n=2, A=benzene ring with $R^5$=hydrogen).

a) 2,3-dihydro-1H,6H-[1,3]thiazino[3,2-a]chinazolin-6-one (structure VI, $R^{11}=R^{12}=R^{13}$=hydrogen, A=benzene ring with $R^5$=hydrogen).
2-ammoniumbenzoic acid methyl ester thiocyanate (5,04 g; 24 mmol) (structure IX, A=benzene ring with $R^5$=hydrogen) is refluxed with 50,0 g 1,2-bromopropane with constant stirring for 150 min. After cooling the reaction mixture, the precipitate is collected, washed with diethylether, and dried. The crude product is dissolved in water and the solution filtered. The filtrate is adjusted to pH 10 with 10% aqueous sodium hydroxide and resulting precipitate collected, washed with water, and dried. The resulting solid is extensively shaken with 30 ml chloroform. The insoluble material is isolated, dried, and recrystallized.
Colorless crystals.
Yield 27% based on 2-ammoniumbenzoic acid methyl ester thiocyanate.
$C_{11}H_{11}N_2OS$ (218,3).
F.: 236° C. (2-methoxyethanol).
IR (ν in $cm^{-1}$): 1600 (C=N), 1632 (C=O), 2926 ($CH_2$), 2956 ($CH_2$).
MS m/e (% B): $M^+$218(100), 190(96), 162(25), 132(46), 118(14).
$UV_{ethanol}$ (in nm) (log ε): 230,4 (4,23), 257,4 (4,37), 305,0 (3,88), 314,6(3,84).

b) From 1,0 g (4,6 mmol) of the compound prepared in (a), 1-(3-mercaptopropyl)-chinazolin-2,4(1H,3H)-dione is prepared by a method analogous to that described in Example 1 d.
Colorless crystals.
Yield 79%.
$C_{11}H_{12}N_2O_2S$ (236,3).
F.: 154°–157° C. (ethanol).
IR (ν in $cm^{-1}$): 1610 (NH), 1682 (C=O), 1702 ($CH_2$), 2544 (SH).
MS m/e (% B): $M^+$236(81), 203(100), 189(10), 176(32), 162(16), 160(26), 146(33), 132(98).
$UV_{ethanol}$ (in nm) (log ε): 220,4 (4,74), 245,2 (4,13), 313,0 (3,87)

EXAMPLE 5

1-(2-mercaptoethyl)-chinazolin-2,4(1H,3H)-dione (structure Ia, $R^1=R^2=R^4$=hydrogen, $R^3$=mercapto, n=1, A=benzene ring with $R^5$=hydrogen).

a) 1,2-dihydro-5H-thiazolo[3,2-a]chinazolin-5-one (structure V, $R^7=R^8=R^9=R^{10}$=hydrogen, A=benzene ring with $R^5$=hydrogen).
The compound, previously described in the literature, is prepared analogously to Example 4 method (a) with 5,04 g (24 mmol) 2-ammonium benzoic acid methyl ester thiocyanate and 50,0 g 1,2-dibromomethane.
Colorless crystals.
Yield 31% based on 2-ammoniumbenzoic add methyl ester thiocyanate.
$C_{10}H_8N_2OS$ (204,3).
F.: 238°–239° C. (2-methoxyethanol).
IR (ν in $cm^{-1}$): 1608 (C=N), 1644 (C=O), 2948 ($CH_2$), 2986 ($CH_2$).
MS m/e (% B): $M^+$204(100), 176(83), 132(38), 104(11).
$UV_{ethanol}$ (in nm) (log ε): 232,8 (4,13), 254,4 (4,21), 308,8 (3,63).

b) 1-(2-mercaptoethyl)-chinazolin-2,4(1H,3H)-dione is prepared analogously to Example 1 (d) from 1,02 g (5,0 mmol) of the compound prepared in (a).
Colorless crystals.
Yield 84%.
$C_{10}H_{10}N_2O_2S$ (223,3).
F.: 178°–181° C. (ethanol).
IR (ν in $cm^{-1}$): 1606 (NH), 1698 asymm. (C=O), 2552 (SH).
MS m/e (% B): $M^+$222(100).
$UV_{ethanol}$ (in nm) (log ε): 220,4 (4,43), 245,2 (3,83), 313,0 (3,57).

EXAMPLE 6

1-(2-mercaptoethyl)-3-methylchinazolin-2,4(1H,3H)-dione (structure Ia, $R^1=R^2$=hydrogen, $R^3$=mercapto, $R^4$ methyl, n=1, A=benzene ring with $R^5$=hydrogen).

1,92 g (10 mmol) of the previously described 3-methyl-chinazolin-4(3H)-on-2(1H)-thione (structure VII, R4=methyl, A=benzene ring with $R^5$=hydrogen) is reacted in 30 ml absolute dimethylformamide with 1,5 g (11 mmol) dry potassium carbonate. With constant stirring, 2,23 g (12 mmol) 1,2-dibromomethane is added dropwise. After 24 h, 150 ml 10% aqueous hydrochloric acid is added, the reaction mixture refluxed for 8, and finally filtered hot. The filtrate is cooled and held for 12 h at ca. 4° C. The resulting precipitate is washed with water, dried, and recrystallized. Thin-layer chromatographically pure 1-(2-mercaptoethyl)-3-methyl-chinazolin-2,4(1H,3H)-dione (780 mg) is obtained.

Colorless crystals.

Yield 33%.

$C_{11}H_{12}N_2O_2S$ (236,3).

F.: 171°–175° C. (ethanol).

IR ($\nu$ in cm$^{-1}$): 1648 (C=O), 1696 (C=O), 2560 (SH), 2942 (CH$_2$).

MS m/e (% B): M$^+$236(13), 189(6), 176(100), 146(7), 132(81), 119(34).

UV$_{etanol}$ (in nm) (log $\epsilon$): 220,5 (4,60), 248,0 (3,88), 311,0 (3,68).

EXAMPLE 7

1-(3-mercaptoprop-1-yl)-3-methyl-chinazolin-2,4(1H,3H)-dione (structure Ia, $R^1=R^2$=hydrogen, $R^3$=mercapto, $R^4$=methyl, n=2, A=benzene ring with $R^5$=hydrogen).

Analogous to Example 6, 1,92 g 10 mmol) 3-methyl-chinazolin-4(3H)-on-2(1H)-thione is reacted with 2,42 g (12 mmol) 1,3-dibromopropane. Thin-layer chromatographically pure 1-(2-mercaptoprop-1-yl)$_3$-methyl-chinazolin-2,4(1H,3H)-dione (525 mg) is obtained.

Colorless crystals.

Yield 21%.

$C_{12}H_{14}N_2O_2S$ (250,3).

F.: 105°–107° C. (ethanol).

IR ($\nu$ in cm$^{-1}$): 1640 (C=O), 1700 (C=O), 2542 (SH), 2932 (CH$_2$).

MS m/e (% B): M$^+$250(65), 217(83), 203(9), 190(30), 176(13), 160(27), 146(35).

EXAMPLE 8

3-ethyl-1-(2-mercaptoethyl)-chinazolin-2,4(1H,3H)-dione (structure Ia, $R^1=R^2$=hydrogen, $R^3$=mercapto, $R^4$=ethyl, n=1, A=benzene ring with $R^5$=hydrogen).

Analogous to Example 6, 2,06 g (10 mmol) of the previously described 3-ethyl-chinazolin-4(3H)-on-2(1H)-thione is reacted with 2,23 g (12 mmol) 1,2-dibromomethane. Thin-layer chromatographically pure 3-ethyl-1-(2-mercaptoethyl)-chinazolin-2,4(1H,3H) dione (475 mg) was obtained.

Colorless crystals.

Yield 19%.

$C_{12}H_{14}N_2O_2S$ (250,3).

F.: 114°–115° C. (ethanol).

IR ($\nu$ in cm$^{-1}$): 1660 (C=O), 1696 (C=O), 2569 (SH).

MS m/e (% B): M$^+$250(11), 203(6), 190(64), 162(41), 146(16), 132(100).

EXAMPLE 9

3-ethyl-1-(3-mercaptoprop-1-yl)-chinazolin-2,4(1H,3H)-dione (structure a, $R^1=R^2$=hydrogen, $R^3$=mercapto, $R^4$=ethyl, n=2, A=benzene ring with $R^5$=hydrogen).

Analogous to Example 6, 2,06 g (10 mmol) of the previously described 3-ethyl-chinazolin-4(3H)-on-2(1H)-thione is reacted with 2,42 g (12 mmol) 1,2-dibromopropane. Thin-layer chromatographically pure 3-ethyl-1-(3-mercaptoprop-1-yl)-chinazolin-2,4(1H,3H)-dione (607 mg) was obtained.

Colorless crystals.

Yield 23%.

$C_{13}H_{16}N_2O_2S$x$H_2O$ (264,3+x$H_2O$).

F.: 110°–114° C. (ethanol).

IR ($\nu$ in cm$^{-1}$): 1652 (C=O), 1702 (C=O), 2562 (SH), 2932 (CH$_2$).

MS m/e (% B): M$^+$264(55), 231(67), 217(8), 203(16), 176(42), 160(23), 146(45).

UV$^{ethanol}$ (in nm) (log $\epsilon$): 222,2 (4,75), 244,0 (4,08), 313,0 (3,87).

EXAMPLE 10

6,7-dimethoxy-1-(2-mercaptoethyl)-3-methyl-chinazolin-2,4(1H,3H)-dione (structure Ia, $R^1=R^2$=hydrogen, $R^3$=mercapto, $R^4$=methyl, n=1, A=benzene ring with $R^5$ in the 6- and 7-positions each —OCH$_3$).

Analogous to Example 6, 2,52 g (10 mmol) of the previously described 6,7-dimethoxy-3-methyl-chinazolin-4(3H)-on-2(1H)-thione is reacted with 2,23 g (12 mmol) 1,2-dibromomethane. Thin-layer chromatographically pure 6,7-dimethoxy-1-(2-mercaptoethyl)-3-methyl-chinazolin-2,4(1H,3H)-dione (1,36 g) was obtained.

Colorless crystals.

Yield 46%.

$C_{13}H_{16}N_2O_4S$ (296,3).

F.: 121°–122° C. (ethanol).

IR ($\nu$ in cm$^{-1}$): 1650 (C=O), 1696 (C=O), 2550 (SH), 2936 (CH$_2$).

MS m/e (% B): M$^+$296(52), 236(100), 221(43), 192(89), 164(18), 149(20), 134(13).

UV$_{ethanol}$ (in nm) (log $\epsilon$): 237,0 (4,59), 259,5 (3,95), 322,0 (3,84).

EXAMPLE 11

3-benzyl-1-(2-mercaptoethyl)-chinazolin-2,4(1H,3H)-dione (structure Ia, $R^1=R^2$=hydrogen, $R^3$=mercapto, $R^4$=benzyl, n=1, A=benzene ring with $R^5$=hydrogen).

Analogous to Example 6, 2,68 g (10 mmol) of the previously described 3-benzyl-chinazolin-4(3H)-on-2(1H)-thione is reacted with 2,23 g (12 ibmol) 1,2-dibromomethane. Thin-layer chromatographically pure 3-benzyl-1-(2-mercaptoethyl)-chinazolin-2,4(1H,3H)-dione (905 mg) was obtained.

Colorless crystals.

Yield 29%.

$C_{17}H_{16}N_2O_2S$ (312,4).

F.: 111°–114° C. (ethanol).

IR ($\nu$ in cm$^{-1}$): 1656 (C=O), 1698 (C=O), 2573 (SH).

MS m/e (% B): M$^+$312(13), 252(93), 235(7), 146(23), 132(100).

UV$_{ethanol}$(in nm) (log $\epsilon$): 223,0 (4,81), 246.2 (4,15), 311,8 (3,84).

EXAMPLE 12

3-(4-mercaptobut-1-yl)-chinazolin-2,4(1H,3H)-dione (structure Ib, Alk*=n-butylene [—(CH$_2$)$_4$-, X=mercapto, A=benzene ring with $R^5$=hydrogen).

a) 3-(4-hydroxybut-1-yl)-chinazolin-4(3H)-on-2(1H)-thione.

(structure XI, A=benzene ring with $R^5$=hydrogen).

9,65 g (0,05 mol) of the previously described 2-isothiocyanate benzoic acid methyl ester (structure X, Alk=methyl, A=benzene ring with $R^5$=hydrogen) is reacted with 4,45 g (0,05 mol) 4-aminobutan-1-ol. The reaction mixture is stirred for 24 h at room temperature, then 40 ml water is added. The resulting precipitate is collected on a glass frit, washed with water, and after drying, recrystallized to obtain 10,6 g 3-(4-hydroxybut-1-yl)-chinazolin-4(3H)-on-2(1H)-thione.
Colorless crystals.
Yield 85%.
$C_{12}H_{14}N_2O_2S \times 0,5H_2O$ (250,3+9,0).
F.: 168°–172° C. (ethanol).
IR ($\nu$ in cm$^{-1}$): 1622 (NH), 1652 (C=O), 2950 (CH$_2$), 3408 (OH).
MS m/e (% B): M$^+$+1 251(100).

b) 2,3,4,5-tetrahydro-7H-[1,3]thiazepino[2,3-b]chinazolin-7-one (structure XII, A=benzene ring with $R^5$=hydrogen).

5,0 g (0,02 mol) of the thin-layer chromatographically pure compound described in (a) is taken up in 35 ml concentrated hydrochloric acid and refluxed for 90 min. After cooling, the precipitate is collected by filtration, and sufficient 5% sodium carbonate is added to obtain pH 8. The precipitate is washed with water, dried, and recrystallized to obtain 3,8 g 2,3,4,5-tetrahydro-7H-[1,3]thiazepino[2,3-b]chinazolin-7-one.
Colorless crystals.
Yield 82%.
$C_{12}H_{12}N_2OS$ (232,3).
F.: 116°–118° C. (ethanol).
IR ($\nu$ in cm$^{-1}$): 1604 (C=N), 1668 (C=O), 2960 (CH$_2$).
MS m/e (% B): M$^+$232(21), 217(100), 199(54), 179(34), 162(69), 146(30), 119(43).
UV$_{ehtanol}$ (in nm) (log $\epsilon$): 226,0 (4,3B), 295,5 (4,16).

c) 3-(4-mercaptobut-1-yl)-chinazolin-2,4(1H,3H)-dione (structure Ib, Alk*=n-butylene [—(CH$_2$)$_4$-], X=mercapto, A=benzene ring with $R^5$=hydrogen).

1,50 g (6,45 mol) of the compound described in (b) is taken up in a mixture of 0,6 ml concentrated sulfuric acid, 1,5 ml glacial acetic acid, and 66 ml water and refluxed for 8 h. After cooling, the precipitate is collected on a glass frit, washed with a small amount of water, dried, and recrystallized to obtain 1,43 g 3-(4-mercaptobut-1-ylchinazolin-2,4(1H,3H)-dione
Colorless crystals.
Yield 89%.
$C_{12}H_{14}N_2O_2S$ (250,3).
F.: 157°–160° C. (ethanol).
IR ($\nu$ in cm$^{-1}$): 1606 (NH), 1664 (C=O), 1712 (C=O), 2573 (SH), 2936 (CH$_2$).
MS m/e (% B): M$^+$250(11), 217(51), 203(3), 187(4), 163(100), 146(76), 119(35).
UV$_{ethanol}$ (in nm) (log $\epsilon$): 219,5 (4,67), 244,0 (3,97), 310,5 (3,65)

EXAMPLE 13

3-(5-mercaptopent-1-yl)-chinazolin-2,4(1H,3H)-dione (structure Ib, Alk*=n-pentylene [—(CH$_2$)$_5$-], X=mercapto, A=benzene ring with $R^5$ hydrogen).

a) 3-(5-hydroxypent-1-yl)-chinazolin-2,4(1H,3H)-dione (structure XV, Alk*=n-pentylene [—(CH$_2$)$_5$—], A=benzene ring with $R^5$=hydrogen).

6,27 (0,03 mol) of the previously described 2-methoxycarbonylaminobenzoic acid methyl ester (structure XIII, Alk=in each case methyl, A=benzene ring with $R^5$=hydrogen) is refluxed with 5,15 g (0,05 mol) 5-aminopentan-1-ol (structure XIV, Alk*=n-pentylene [—(CH$_2$)$_5$-]) for 10 min with moderate heating. After cooling, 100 ml water is added with stirring, and finally sufficient dilute hydrochloric acid is added to ca. pH 4. The crude product is crystallized by the addition of a small amount of ethanol to yield, after filtration and drying, 6,18 g 3-(5-hydroxypent-1-yl)-chinazolin-2,4(1H,3H)-dione.
Colorless crystals.
Yield 83%.
$C_{13}H_{16}N_2O_3 \times 1H_2O$ (248,3+18,0).
F.: 125°–129° C. (ethanol/water).
IR ($\nu$ in cm$^{-1}$): 1632 asymm. (NH, C=O), 1720 (C=O), 2936 (CH$_2$).
MS m/e (% B): M$^+$248(10), 231(8), 218(20, 176(35, 163(100), 146(77), 119(56).

b) 3-(5-bromopent-1-yl)-chinazolin-2,4(1H,3)-dione (structure XVI, Alk*=n-pentylene [—(CH$_2$)$_5$-], Hal=bromine, A=benzene ring with $R^5$=hydrogen).

2,48 g (0,01 mol) of the thin-layer chromatographically pure compound prepared in (a) is taken up in 25 ml concentrated hydrobromic acid and heated to reflux for 30 min. After cooling, the precipitate is collected by filtration and dried to yield 2,89 g thin-layer chromatographically pure 3-(5-bromopent-1-yl)-chinazolin-2,4(1H,3H)-dione.
Colorless needles.
Yield 93%.
$C_{13}H_{15}N_2O_2Br$ (311,2).
F.: 169°–172° C. (ethanol).
IR ($\nu$ in cm$^{-1}$): 1622 (NH), 1666 (C=O), 1712 (C=O), 2940 (CH$_2$).
MS m/e (% B): M$^+$+1 313(96,311(100).

c) 3-(5-mercaptopent-1-yl)-chinazolin-2,4(1H,3H)-dione (structure Ib, Alk*=n-pentylene [—(CH$_2$)$_5$-], X=mercapto, A=benzene ring with $R^5$=hydrogen).

1,55 g (5,0 mmol) of the compound prepared in (b) is taken up in 5 ml 2-methoxyethanol, to which is added 0,46 g (6 mmol) thiourea. The reaction mixture is refluxed for 30 min. After cooling, 50 ml water is added and sufficient 4% aqueous sodium hydroxide to achieve alkaline pH., After the solution clears, it is filtered and then acidified with 10% aqueous hydrochloric acid. The precipitate is collected, washed, and dried to yield 780 mg 3-(5-mercaptopent-1-yl)-chinazolin-2,4(1H,3H)-dione.
Colorless crystals.
Yield 59%.
$C_{13}H_{16}N_2O_2S$ (264,3).
F.: 137°–138° C. (ethanol).
IR ($\nu$ in cm$^{-1}$): 1636 asymm. (NH, C=O), 1726 (C=O), 2585 (SH), 2936 (CH$_2$).
MS m/e (% B): M+264(9), 231(46), 176(10), 163(100), 146(48), 119(26).
UV$_{ethanol}$ (in nm) (log $\epsilon$): 220,0 (4,91), 243,5 (4,23), 310,8 (3,93).

EXAMPLE 14

1-(3-mercaptoprop-1-yl)-3-methyl-thieno(3,2-d)-pyrimidin-2,4(1H,3H)-dione
(structure Ia, $R^1=R^2$=hydrogen, $R^3$ mercapto, $R^4$=methyl, n=2, A=2,3-annealed thiophene ring).

Analogous to example 6, 0,99 g (5 mmol) of the previously described 3-methyl-thieno[3,2d]-pyrimidin-4(3H)-on-2(1H)-thione is reacted with 1,11 g (5,5 mmol) 1,3-dibromopropane and 0,75 g (5,4 mmol) potassium carbonate in 15 ml absolute dimethylformamide. After 2 h, 60 ml 10% hydrochloric acid is added and the mixture refluxed for an additional 3 h to yield 1,14 g thin-layer chromatographically pure 1-(3-mercaptoprop-1-yl)-3-methyl-thieno(3,2-d)-pyrimidin-2,4(1H,3H)-dione.
Ochre crystals.
Yield 89%.
$C_{10}H_{12}N_2O_2S_2$ (264,3).
F.: 174°–176° C. (ethanol).

IR (ν in cm$^{-1}$): 1660 (C=O), 1691 (C=O), 2560 (SH).
MS m/e (% B): M$^+$256(100), 223(50), 196(39), 152(40), 138(93), 125(23), 110(24).
UV$_{ethanol}$ (in nm) (log ε): 219,6 (0,42), 273,7 (3,23), 306,2 (3,42).

EXAMPLE 15

Tablets with 50,0 mg 1-(3-mercaptoprop-1-yl)-3-methyl-chinazolin-2,4(1H,3H)-dione Components:

1 tablet contains 50,0 active substance, 32,0 mg microcrystalline cellulose, 20,0 mg lactose, 15, 0 mg potato starch, 8,0 mg talc, 3,2 mg polyvinylpyrrolidone, and 1,5 mg magnesium stearate.

Preparation:

The powdered active substance is mixed to homogeneity with microcrystalline cellulose, lactose, and potato starch in a 20% w/v solution of polyvinylpyrrolidone in ethanol. The moist mass is pressed through a 1,5-mm mesh seive, dried at 40° C., and again pressed through a 1,0-mm mesh seive. The resulting granulate is mixed with talc and magnesium stearate and pressed into tablets.

Tablet weight: 130 mg.

EXAMPLE 16

Coated Tablets with 35 mg 1-(3-mercaptoprop-1-yl)-chinazolin-2,4(1H,3H)-dione

Components:

One coated tablet contains 35 mg active substance, 20,0 mg microcrystalline cellulose, 10,0 mg lactose, 16,5 mg cornstarch, 5,0 mg talc, 2,8 mg polyvinylpyrrolidone, and 0,7 mg magnesium stearate.

Preparation:

The powdered active substance is mixed to homogeneity with microcrystalline cellulose, lactose, and cornstarch in a 20% w/v solution of polyvinylpyrrolidone in ethanol. The moist mass is pressed through a 1,5-mm mesh seive, dried at 40° C., and again pressed through a 1,0-mm mesh seive. The resulting granulate is mixed with talc and magnesium stearate and pressed into tablet cores.

Core weight: 90 mg.

The tablet or suppository cores as described are coated and polished by standard methods.

EXAMPLE 17

1-(2-mercaptoethyl)-3-methyl-thieno[3,2-d]-pyrimidine-2,4 (1H,3H)-dione (structure Ia, R$^1$, R$^2$=hydrogen, R$^3$=mercapto, R$^4$=methyl, n=1, A=2,3-annealed thiophene ring).

Analogous to example 14, 0,99 g (5 mmol) of the previously described 3-methyl-thieno[3,2-d]-pyrimidin-4(3H)-on-2(1H)-thione is reacted with 1,03 g (5,5 mmol) 1,2-dibromomethane to produce 420 mg thin-layer chromatographically pure 1-(2-mercaptoethyl)-3-methyl-thieno[3,2-d]-pyrimidine-2,4(1H,3H)-dione.

Ochre crystals.
Yield 41%.
C$_9$H$_{10}$N$_2$O$_2$S$_2$ (242,3).
F.: 158°–160° C. (ethanol).
IR (ν in cm$^{-1}$): 1648 (C=O), 1692 (C=O), 2590 (SH).
MS m/e (% B): M$^+$242(27), 183(83), 138(100), 125(32), 110(18).
UV$_{ethanol}$ (in nm) (log ε): 222,5 (4,20), 270,8 (2,78), 316,7 (3,05).

EXAMPLE 18

(R,S)-3-[3-(1-methyl)-mercaptopropyl]-chinazolin-2,4 (1H,3H)-dione (structure Ib, Alk*=1-methyl-propyl, X=3-mercapto, A=annealed benzene ring with R$^5$=hydrogen).

a) 2-crotylthiochinazolin-4(3H)-one

The previously described compound is prepared in thin-layer chromatographically pure form from 3,56 g (20 mmol) chinazolin-4(3H)-on-2(1H)-thione and 1,81 g (20 mmol) crotyl chloride.

Colorless crystals.
Yield 71%.
C$_{12}$H$_{12}$N$_2$OS (232,3).
F.: 193°–194° C. (ethanol).
IR (ν in cm$^{-1}$): 1613 (C=N), 1673 (C=O), 2953 (CH$_2$).
MS m/e (% B): M$^+$+1 233(100).
UV$_{ethanol}$ (in nm) (log ε): 230,5 (4,47), 274,5 (4,24), 314,5 (3,84).

b) (R,S)-4-methyl-3,4-dihydro-2H,6H-[1,3]thiazino[2,3-b] chinazolin-6-one 1,15 g (5 mmol) of the compound obtained in (a) is taken up in 5 ml concentrated sulfuric acid and stirred for 2 h at 40° C. After this, 100 ml ice-cold water is added and saturated sodium carbonate, and if necessary 1N aqueous sodium hydroxide, is added to neutrality. The resulting precipitate is collected, dried, and recrystallized.

Colorless crystals.
Yield 51%.
C$_{12}$H$_{12}$N$_2$OS (232,3).
F.: 111°–112° C. (ethanol).
IR (ν in cm$^{-1}$): 1608 (C=N), 1678 (C=O), 2938 (CH$_2$).
MS mile (% B): M$^{+232}$(100).
UV$_{ethanol}$(in nm) (log ε): 235,0 (4,32), 283,8 (4,15).

c) (R,S)-3-[3-(1-methyl)-mercaptopropyl]-chinazolin-2,4 (1H,3H)-dione (structure Ib, Alk*=1-methyl-propyl, X=3mercapto, A=annealed benzene ring with R$^5$=hydrogen).

Analogous to example 1, step 1d, 0,5 g (2 mmol) thiazo-compound (b) is taken up in the acid mixture, heated to reflux, and finally recrystallized.

Colorless crystals.
Yield 71%.
C$_{12}$H$_{12}$N$_2$O$_2$S (232,3).
F.: 114°–118° C. (ethanol).
IR (ν in cm$^{-1}$), 1620 (NH), 1644 (C=O), 1720 (C=O), 2562 (SH).
MS m/e (% B): M$^+$250(11), 232(13), 217(96), 201(14), 163(100), 146(79), 119(26), 90(29).
UV$_{ethanol}$ (in nm) (log ε): 220,0 (4,67), 242,0 (4,10), 313,0 (3,87).

EXAMPLE 19

(R,S)-3-[3-(2-methyl)-mercaptopropyl]chinazolin-2,4(1H, 3H)-dione (structure Ib, Alk*=2-methyl-propyl, X=3-mercapto, A=annealed benzene ring with R$^5$=hydrogen).

a) (R,S)-3-methyl-3,4-dihydro-2H,6H-[1,3]thiazino[2,3-b]-chinazolin-6-one 3,65 g (20 mmol) of the previously described compound chinazolin-4(3H)-on-2(1 H)-thione and 2,6 g (20 mmol) potassium carbonate are mixed in 30 ml dimethylformamide. After dissolution of the chinazoline, 2,19 g (22 mmol) 1-chloro-3-bromo-2-methylpropane is added and the mixture shaken for 2 days. The precipitate is recovered and recrystallized.

Colorless crystals.
Yield 79%.
C$_{12}$H$_{12}$N$_2$OSxH$_2$O (232,3+xH$_2$O).

F.: 141°–146° C. (ethanol).
IR (ν in cm$^{-1}$): 1606 (C=N), 1682 (C=O), 2932 (CH$_2$).
MS m/e (% B): M$^+$232(100), 217(38), 199(26), 162(46).
UV$_{ethanol}$(in nm) (log ε): 237,0 (4,28), 290,5 (4,25).
b) (R,S,)-3-(3-(2-methyl(-mercaptopropyl]chinazolin-2,4 (1H,3H)-dione
(structure Ib, Alk*=2-methyl-propyl, X=3-mercapto, A=annealed benzene ring with R$^5$=hydrogen).
Analogous t6 example 1, step 1d, 0,5 g of the compound described in (a) was used.
Colorless crystals.
Yield 79%.
C$_{12}$H$_{12}$N$_2$OSxH$_2$O (232,3+xH$_2$O).
F.: 194°–197° C. (ethanol).
IR (ν in cm$^{-1}$): 1640 asymm. (NH, C=O), 1722 (C=O), 2572 (SH).
MS m/e (% B): M$^+$250(24), 217(100), 201(17), 176(43), 163(57), 146(84), 119(47), 90(25).
UV$_{ethanol}$ (in nm) (log ε): 219,4 (4,66), 240,0 (4,12), 293,0 (3,99).

EXAMPLE 20

N-hydroxy-2-[3-(methyl-2,4-dioxo-3,4-dihydro-2H-chinazolin-1-yl)-propylsulfanyl]acetamide
(structure Ia, R$^1$=R$^2$=hydrogen, R$^3$=hydroxycarbamoylmethylenethio, R$^4$=methyl, n=2, A=benzene ring with R$^5$=hydrogen).
250 mg (1 mmol) 1-(3-mercaptoprop-1-yl)-3-methyl-chinazolin-2,4(1H,3H dione (as in example 7) is dissolved in 4 ml absolute dimethylformamide under nitrogen. Then, 330 mg (3 mmol) 2-chloro-N-hydroxyacetamide and 0,83 ml (6 mmol) triethylamine are added and the mixture stirred under nitrogen for 3 h. After the addition of 1 ml water, on ice, the mixture is acidified with glacial acetic acid and stirred at 0° C. for an additional 2 h. The precipitated solid is collected, washed with water, dried, and recrystallized.
Colorless crystals.
Yield 66%.
Cl$_4$H$_{17}$N$_3$O$_4$S (323,4).
F.: 146°–148° C. (ethyl acetate/petroleum ether).
IR (ν in cm$^{-1}$): 1488 (C=O), 1646 (C=O), 1697 (C=O), 3200–3500 (OH).
MS m/e (% B): M$^+$323(5), 264(5), 250(50), 217(35).
UV$_{ethanol}$ (in nm) (log ε): 215,4 (4,26), 302,1 (3,04), 332,9 (2,71).

What is claimed is:

1. A method of inhibiting collagenase/MMP activities in a mammal comprising administering to the mammal in need thereof an effective amount of one or more polycyclic (pyrimidine-2,4(1H, 3H)-diones) with functionalized alkyl groups in the 1-, 3-, or both positions with the general structures Ia and Ib,

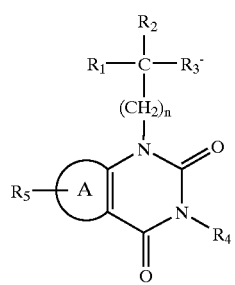

(Ia)

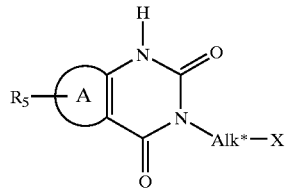

(Ib)

where:

R$^1$ is hydrogen, methyl, or ethyl;
R$^2$ is hydrogen or methyl;
R$^3$ is mercapto or hydroxyaminoacylalkylthio (—SAlkCONHOH);
Alk is C$_1$–C$_5$ branched or unbranched alkyl;
R$^4$ is hydrogen, benzyl, or phenyl;
n is 0, 1 or 2;
Alk* is C$_2$–C$_{12}$ branched or unbranched alkylene, with the exception of 3-methylpropylene [—CH$_2$—CH$_2$—CH(CH$_3$)-];
X is mercapto or hydroxyaminoacylalkylthio (—SAlkCONHOH);
A is an annealed benzene ring or a 2,3-annealed thiophene ring, wherein the 4,5-positions are optionally substituted with methyl groups or are optionally annealed with a cyclopentene, cyclohexene, or cycloheptene ring,
R$^5$ is hydrogen, 6-methyl, 8-methyl, 6-fluoro, 6-choloro, 6-bromo, 6-methylthio, or 6,7-dimethoxy,
as well as the tautomers and pharmacologically relevant salts of these compounds.

2. A method of inhibiting tumor metastasis and invasion in a mammal comprising administering to the mammal in need thereof an effective amount of one or more polycyclic (pyrimidine-2,4(1H, 3H)-diones) with functionalized alkyl groups in the 1-, 3-, or both positions with the general structures Ia and Ib,

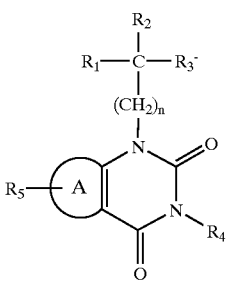

(Ia)

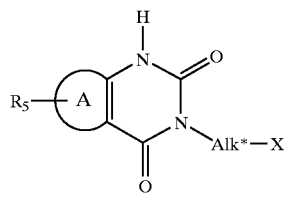

(Ib)

where:

R$^1$ is hydrogen, methyl, or ethyl;
R$^2$ is hydrogen or methyl;

$R^3$ is mercapto or hydroxyaminoacylalkylthio (—SAlkCONHOH);

Alk is $C_1$–$C_5$ branched or unbranched alkyl;

$R^4$ is hydrogen, benzyl, or phenyl;

n is 0, 1 or 2;

Alk* is $C_2$–$C_{12}$ branched or unbranched alkylene, with the exception of 3-methylpropylene [—$CH_2$—$CH_2$—$CH(CH_3)$—], X is mercapto or hydroxyaminoacylalkylthio (—SAlkCONHOH);

A is an annealed benzene ring or a 2,3-annealed thiophene ring, wherein the 4,5-positions are optionally substituted with methyl groups or are optionally annealed with a cyclopentene, cyclohexene, or cycloheptene ring, $R^5$ is hydrogen, 6-methyl, 8-methyl, 6-fluoro, 6-choloro, 6-bromo, 6-methylthio, or 6,7-dimethoxy, as well as the tautomers and pharmacologically relevant salts of these compounds.

3. A method of treating UV-induced erythema in a mammal comprising administering to the mammal in need thereof an effective amount of one or more polycyclic (pyrimidine-2,4(1H, 3H)-diones) with functionalized alkyl groups in the 1-, 3-, or both positions with the general structures Ia and Ib,

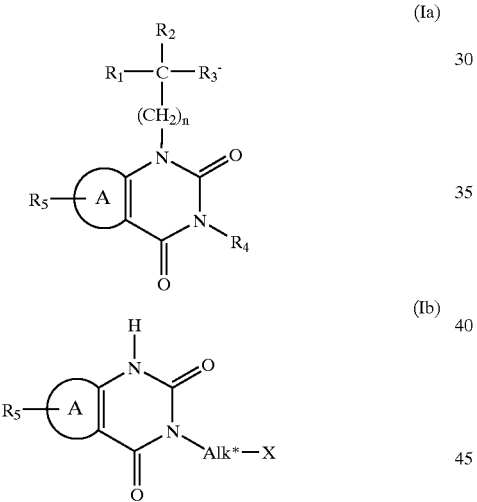

where:

$R^1$ is hydrogen, methyl, or ethyl;

$R^2$ is hydrogen or methyl;

$R^3$ is mercapto or hydroxyaminoacylalkylthio (—SAlkCONHOH);

Alk is $C_1$–$C_5$ branched or unbranched alkyl;

$R^4$ is hydrogen, benzyl, or phenyl;

n is 0, 1 or 2;

Alk* is $C_2$–$C_{12}$ branched or unbranched alkylene, with the exception of 3-methylpropylene [—$CH_2$—$CH_2$—$CH(CH_3)$—];

X is mercapto or hydroxyaminoacylalkylthio (—SAlkCONHOH);

A is an annealed benzene ring or a 2,3-annealed thiophene ring, wherein the 4,5-positions are optionally substituted with methyl groups or are optionally annealed with a cyclopentene, cyclohexene, or cycloheptene ring, $R^5$ is hydrogen, 6-methyl, 8-methyl, 6-fluoro, 6-choloro, 6-bromo, 6-methylthio, or 6,7-dimethoxy, as well as the tautomers and pharmacologically relevant salts of these compounds.

4. A method of treating rheumatic diseases in a mammal comprising administration to the mammal in need thereof an effective amount of one or more polycyclic (pyrimidine-2,4(1H, 3H)-diones) with functionalized alkyl groups in the 1-, 3-, or both positions of the general structures Ia and Ib,

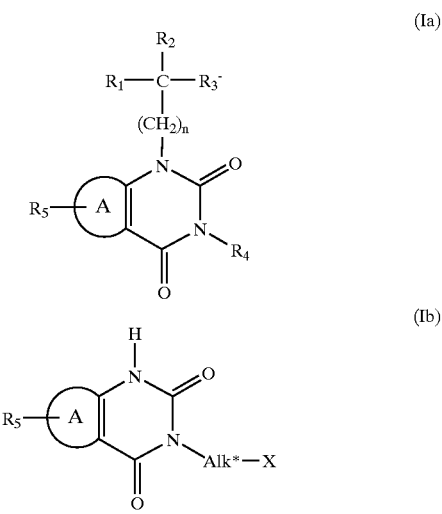

where:

$R^1$ is hydrogen, methyl, or ethyl;

$R^2$ is hydrogen or methyl;

$R^3$ is mercapto or hydroxyaminoacylalkylthio (—SAlkCONHOH);

Alk is $C_1$–$C_5$ branched or unbranched alkyl;

$R^4$ is hydrogen, benzyl, or phenyl;

n is 0, 1 or 2;

Alk* is $C_2$–$C_{12}$ branched or unbranched alkylene, with the exception of 3-methylpropylene [—$CH_2$—$CH_2$—$CH(CH_3)$—];

X is mercapto or hydroxyaminoacylalkylthio (—SAlkCONHOH);

A is an annealed benzene ring or a 2,3-annealed thiophene ring, wherein the 4,5-positions are optionally substituted with methyl groups or are optionally annealed with a cyclopentene, cyclohexene, or cycloheptene rine, $R^5$ is hydrogen, 6-methyl, 8-methyl, 6-fluoro, 6-choloro, 6-bromo, 6-methylthio, or 6,7-dimethoxy, as well as the tautomers and pharmacologically relevant salts of these compounds.

5. The method of claim 1, wherein the one or more polycyclic (pyrimidine-2,4(1H, 3H)-diones) are compounds of the general structures IIa and IIb

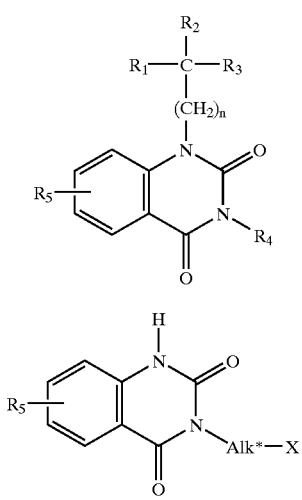

(IIa)

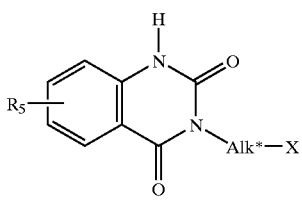

(IIb)

where

R¹, R², R³, R⁴, R⁵, Alk, Alk*, n, and X are defined as in claim 1, including their tautomers and pharmacologically relevant salts.

6. The method of claim 2, wherein the one or more polycyclic (pyrimidine-2,4(1H, 3H)-diones) are compounds of the general structures IIa and IIb (IIa)

(IIb)

where

R¹, R², R³, R⁴, R⁵, Alk, Alk*, n, and X are defined as in claim 2, including their tautomers and pharmacologically relevant salts.

7. The method of claim 3, wherein the one or more polycyclic (pyrimidine-2,4(1H, 3H)-diones) are compounds of the general structures IIa and IIb

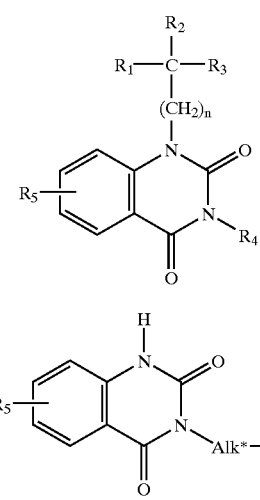

(IIa)

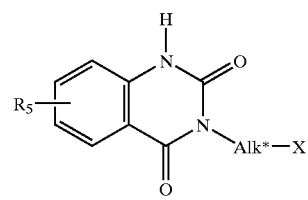

(IIb)

where

R¹, R², R³, R⁴, R⁵, Alk, Alk*, n, and X are defined as in claim 3, including their tautomers and pharmacologically relevant salts.

8. The method of claim 4, wherein the one or more polycyclic (pyrimidine-2,4(1H, 3H)-diones) are compounds of the general structures IIa and IIb

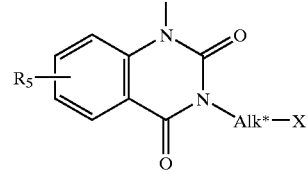

(IIa)

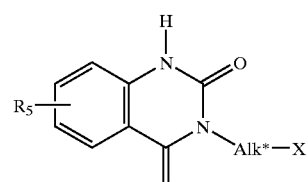

(IIb)

where

R¹, R², R³, R⁴, R⁵, Alk, Alk*, n, and X are defined as in claim 4, including their tautomers and pharmacologically relevant salts.

* * * * *